(12) United States Patent
Shen et al.

(10) Patent No.: US 8,215,929 B2
(45) Date of Patent: Jul. 10, 2012

(54) DETACHABLE PUMP AND THE NEGATIVE PRESSURE WOUND THERAPY SYSTEM USING THE SAME

(75) Inventors: Te-Yang Shen, Hsinchu County (TW); Nan-Kuang Yao, Taoyuan County (TW)

(73) Assignee: Industrial Technology Research Institute, Hsin-Chu (TW)

( * ) Notice: Subject to any disclaimer, the term of this patent is extended or adjusted under 35 U.S.C. 154(b) by 771 days.

(21) Appl. No.: 12/101,946

(22) Filed: Apr. 11, 2008

(65) Prior Publication Data

US 2009/0125004 A1    May 14, 2009

(30) Foreign Application Priority Data

Nov. 9, 2007  (TW) .............................. 96142335 A

(51) Int. Cl.
*F04B 17/00*    (2006.01)
(52) U.S. Cl. ..................... 417/413.1; 417/360
(58) Field of Classification Search ............... 417/412, 417/413.1, 413.2, 413.3, 415, 416, 417; 310/15, 310/17, 23; 251/129.17
See application file for complete search history.

(56) References Cited

U.S. PATENT DOCUMENTS

| | | | |
|---|---|---|---|
| 2,293,542 A * | 8/1942 | Hamilton ...................... 417/44.1 |
| 2,635,552 A * | 4/1953 | Dale et al. ........................ 418/69 |
| 3,230,889 A | 1/1966 | Brewer |
| 3,411,450 A * | 11/1968 | Clifton .......................... 417/420 |
| 3,760,206 A * | 9/1973 | Hertrich ........................... 310/13 |
| 4,370,107 A | 1/1983 | Landis et al. |
| 4,560,326 A * | 12/1985 | Seki .............................. 417/480 |
| 5,065,126 A * | 11/1991 | Suzuki et al. .................. 335/222 |
| 5,154,570 A * | 10/1992 | Yoshikawa et al. ............. 415/24 |
| 5,549,584 A | 8/1996 | Gross |
| 5,636,643 A | 6/1997 | Argenta et al. |
| 5,645,081 A | 7/1997 | Argenta et al. |
| 6,514,047 B2 * | 2/2003 | Burr et al. ........................ 417/53 |
| 6,758,657 B1 | 7/2004 | McNaull et al. |
| 7,216,651 B2 | 5/2007 | Argenta et al. |
| 2007/0055209 A1 | 3/2007 | Patel et al. |
| 2007/0179460 A1 | 8/2007 | Adahan |
| 2007/0265586 A1 | 11/2007 | Joshi et al. |

FOREIGN PATENT DOCUMENTS

DE    202004003514 U1    7/2005
GB          2378734 A    2/2003
(Continued)

OTHER PUBLICATIONS

David G Armstrong et al., Negative pressure wound therapy after partial diabetic foot amputation: a multicentre, randomised controlled trial, Lancet, Nov. 12, 2005, P1704-1710, vol. 366.

(Continued)

*Primary Examiner* — Devon C Kramer
*Assistant Examiner* — Dnyanesh Kasture
(74) *Attorney, Agent, or Firm* — Morris Manning & Martin LLP; Tim Tingkang Xia, Esq.

(57) ABSTRACT

The present invention relates to a detachable pump and a negative pressure wound therapy (NPWT) system using the same. The detachable pump comprises: a top module, including a motor set and a top elastic member; and a bottom module, arranged beneath the top module in a manner that it is connected to the top module by a detachable connection mechanism and comprised of: a base configured with an inlet and an outlet; at least an one-way suction valve; at least an one-way drain valve; a diaphragm element; and a bottom elastic member.

13 Claims, 5 Drawing Sheets

FOREIGN PATENT DOCUMENTS

| | | | |
|---|---|---|---|
| JP | 57212382 | A * | 12/1982 |
| WO | 2007030601 | | 3/2007 |
| WO | 2007030601 | A2 | 3/2007 |
| WO | 2008048527 | | 4/2008 |
| WO | 2008135997 | A2 | 11/2008 |

OTHER PUBLICATIONS

Usopov and Yepifanov (The Kremlin Papers, Russia, 1986-1991).
France Search Report issued on Oct. 5, 2009.
German Office Action issued on Feb. 27, 2009.

* cited by examiner

US 8,215,929 B2

DETACHABLE PUMP AND THE NEGATIVE PRESSURE WOUND THERAPY SYSTEM USING THE SAME

FIELD OF THE INVENTION

The present invention relates to a detachable pump and a negative pressure wound therapy system using the same, and more particularly, to a detachable pump configured with disposable components that can be incorporated into a negative pressure wound therapy (NPWT) system along with dressings and absorbent materials for drawing spent liquid of a wound to be absorbed directly by the absorbent materials by way of the dressings.

BACKGROUND OF THE INVENTION

Negative pressure wound therapy (NPWT) is the use of sub-atmospheric pressure to assist wound healing, or to remove fluids from a wound site. As the conventional NPWT system shown in FIG. 1, the NPWT system comprises: a patch 200 sealing a wound 500; a flexible suction disc (not shown in the figure); a bio-compatible porous wound dressing 300; a drainage tube 310 placed adjacent to or inserted in the dressing 300 for connecting the wound 500 to a spent liquid container 600; and a connection tube 110 connecting the spent liquid container 600 to a vacuum source 100; by which a negative pressure is applied to the wound 500 in the flesh 400. The concept is to turn an open wound into a controlled, closed wound while removing excess fluid from the wound bed, thus enhancing blood circulation and disposal of cellular waste from the lymphatic system for assisting wound healing.

The designing principle of the cascade-like connection of the dressing 300, the spent liquid container 600 and the vacuum source 100 is to prevent the vacuum source 100 from being contamination. However, the aforesaid conventional NPWT has the following shortcomings:

(1) As the spent liquid container 600 is connected to the vacuum source 100 by the connection tube 110 with a length, not only the connection tube 110 is too long may the cause of inconvenience, but also it is difficult to prevent the same from leakage and thus may cause the performance of the vacuum source 100 to drop.

(2) Considering factors such as power, noise, and lifespan, the vacuum source 100 must adopt high-power motor, but the vacuum source 100 using high-power motor not only is overweighted, but is expensive.

(3) As the power consumption of the vacuum source 100 using high-power motor is comparatively higher, larger battery module 700 should be used that further cause the whole NPWT system to be larger and heavier.

(4) As the spend liquid container 600 should be designed with a volume, not only it is lumpy and may take up quit a few space, but also it may cause difficulties for moving the NPWT system.

(5) There can always be a potential hazard that the spent liquid container 600 may be tilted for causing the spent liquid storing therein to pour out and thus contaminate the whole NPWT system.

(6) The aforesaid NPWT system is too large and heavy that it is not portable so as to be carried by a patient.

There are already some studies trying to improve the conventional NPWT system. One of which is an appliance for administering a reduced pressure treatment to a wound, disclosed in U.S. Pat. No. 7,216,651, entitled "Wound treatment employing reduced pressure". However, the aforesaid appliance still adopt the conventional cascade-like connection of the dressing, the spent liquid container and the vacuum source 100 so that it is complex and expensive.

Another such study is an apparatuses for evacuating body fluids, disclosed in U.S. Pat. No. 5,549,584, entitled "Apparatus for removing fluid from a wound". In the aforesaid apparatus, the dressing covering a wound is connected to a bellows pump while the bellows pump is then being connected to a collection bag that is different from the aforesaid conventional NPWT system, i.e. the dressing is connected to the pump and then the pump is connected to the collection bag. It is only suitable for treating wounds with small opening despite of it is ease to operate, since the negative pressure of the aforesaid apparatus is generated by the operation of the bellows pump in a manual manner that can not be controlled accurately.

Yet, another such study is a wound dressing apparatus disclosed in U.S. Pub. No. 2007/0055209, entitled "Self contained wound dressing apparatus". The components used in the apparatus is connected in a manner that is similar to the apparatuses disclosed in U.S. Pat. No. 5,549,584, i.e. the dressing is connected to the pump and then the pump is connected to the collection bag. The difference is that, instead of the bellows pump, the wound dressing apparatus uses an external peristaltic vacuum pump which can only generate a comparatively smaller vacuuming force. Any intension for increasing vacuuming force will require the wound dressing apparatus to use larger external peristaltic vacuum pump, however, it is going to cause the volume of the wound dressing apparatus to increase.

SUMMARY OF THE INVENTION

The object of the present invention is to provide a detachable pump configured with disposable components that can be incorporated into a negative pressure wound therapy (NPWT) system along with dressings and absorbent materials for drawing spent liquid of a wound to be absorbed directly by the absorbent materials by way of the dressings so that not only the piping length and the volume of the NPWT system are reduced, but also the power requirement of the pump is decreased.

To achieve the above object, the present invention provides a detachable pump and a negative pressure wound therapy (NPWT) system using the same. The detachable pump comprises: a top module, including a motor set and a top elastic member; and a bottom module, arranged beneath the top module in a manner that it is connected to the top module by a detachable connection mechanism and comprised of: a base configured with at least a channel; at least an one-way valve installed at an end of the channel for preventing a spent liquid to flow in a direct toward the base; a diaphragm element; and a bottom elastic member; wherein, the spent liquid can be prevented from flowing back to a wound or the base by the one-way valve as the top elastic member is configured to be pushed by the motor set for enabling the resulting resilience of the top elastic member to counter with the resilience of the bottom elastic member in a manner that the diaphragm element is propelled for enabling the detachable pump to generate a vacuuming force; and by incorporating the aforesaid detachable pump into a NPWT system along with dressings and absorbent materials, the spent liquid of a wound is drawn by the pump to be absorbed directly by the absorbent materials by way of the dressings.

Further scope of applicability of the present application will become more apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given herein below and the accompanying drawings which are given by way of illustration only, and thus are not limitative of the present invention and wherein.

DESCRIPTION OF THE EXEMPLARY EMBODIMENTS

For your esteemed members of reviewing committee to further understand and recognize the fulfilled functions and structural characteristics of the invention, several exemplary embodiments cooperating with detailed description are presented as the follows.

Figure 1:
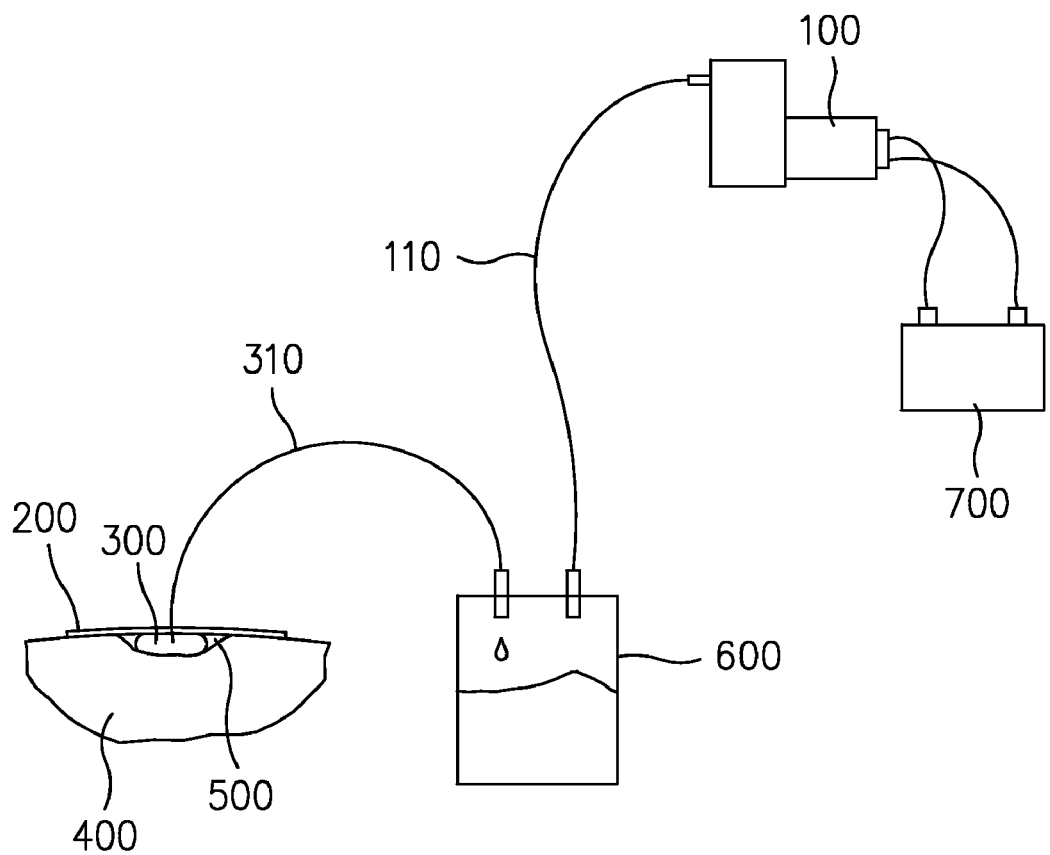
FIG. 1 shows a conventional negative pressure wound therapy system.
Figure 2:
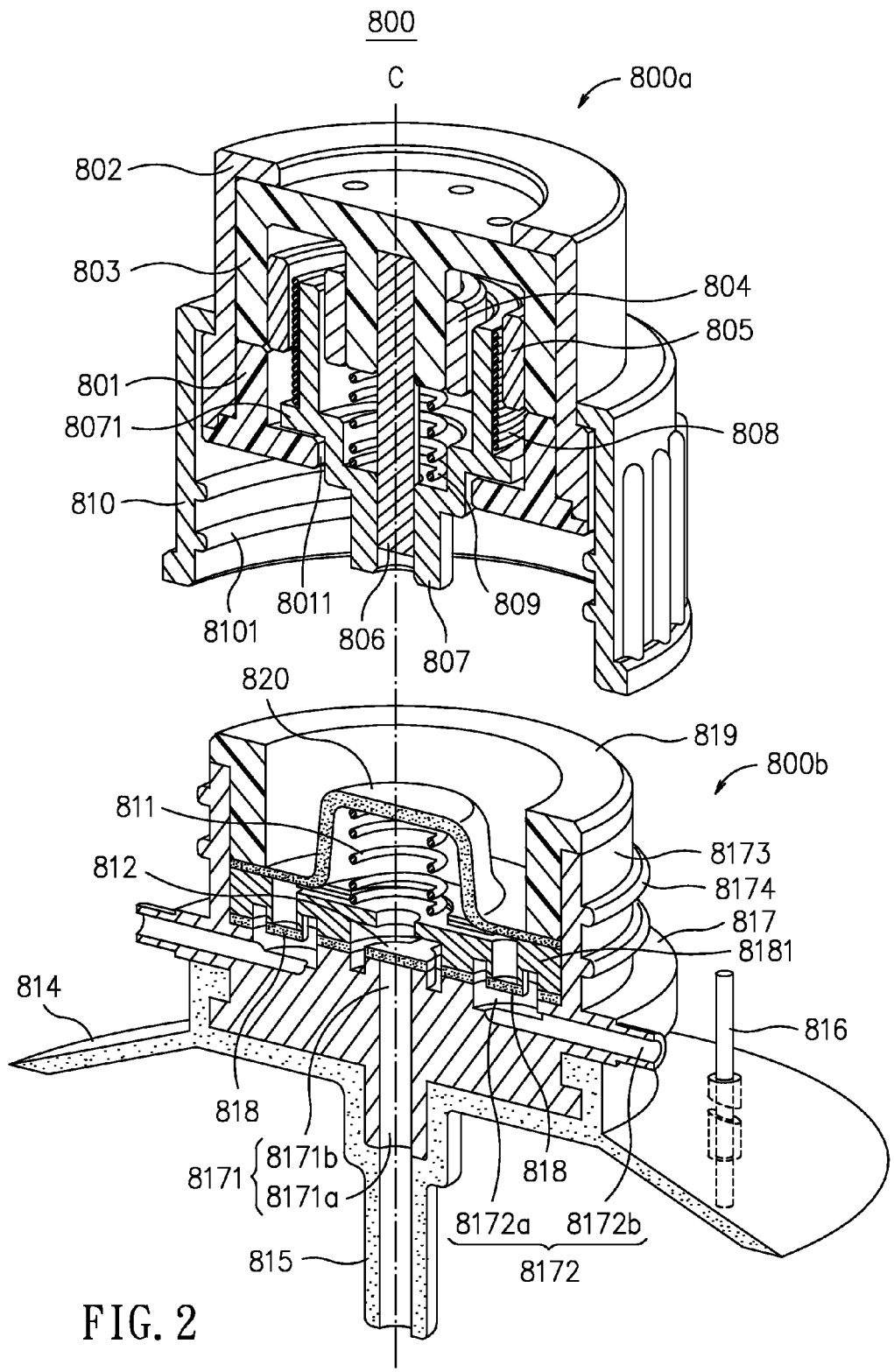
FIG. 2 is a sectional view of a top module and a sectional view of a bottom module of a detachable pump according to an exemplary embodiment of the invention.
Figure 3:
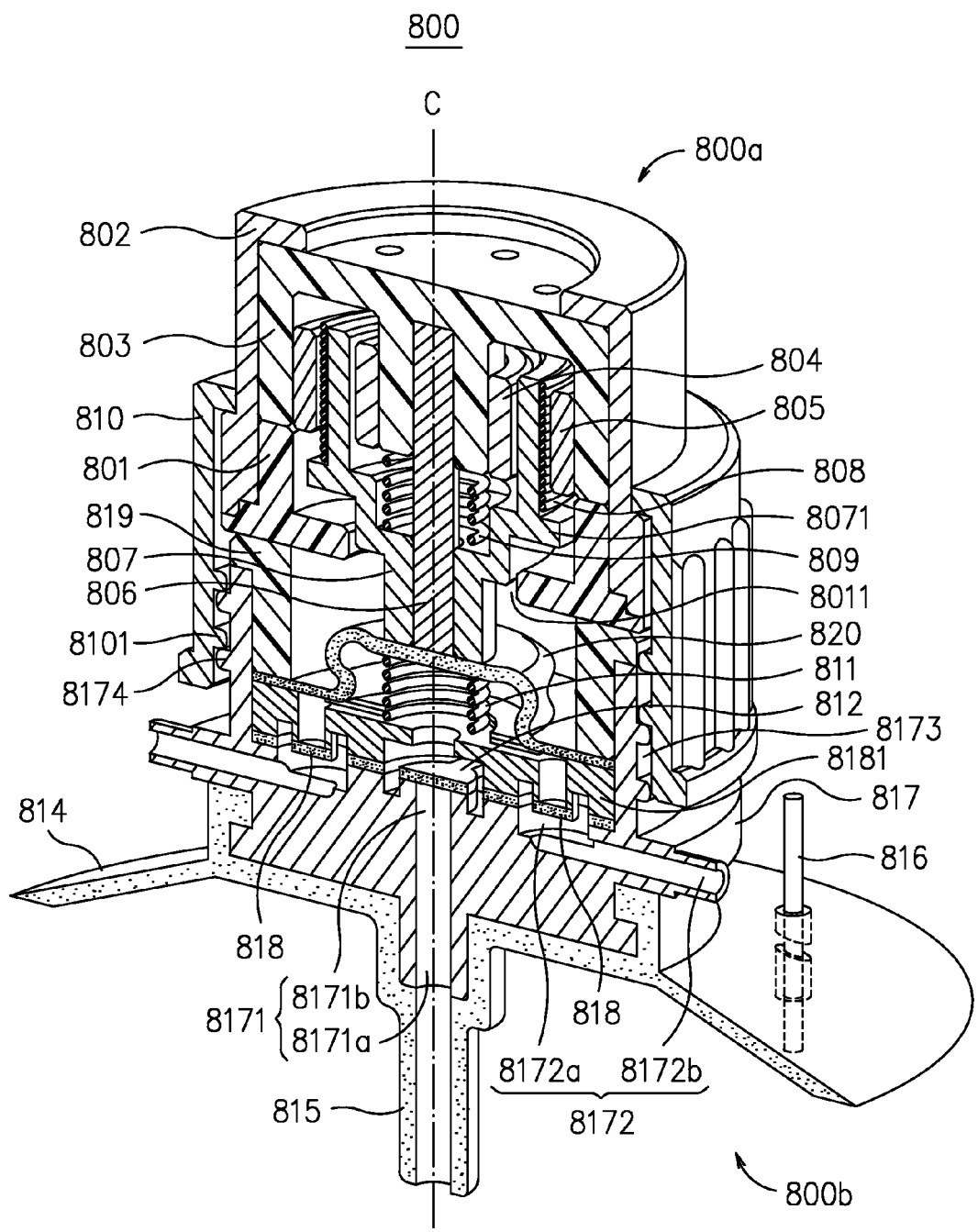
FIG. 3 is a sectional view of a detachable pump according to an exemplary embodiment of the invention.

As shown in FIG. 2 and FIG. 3, the detachable pump 800 of the invention is composed of a top module 800a and a bottom module 800b that can be separated from each other. In which, the top module 800a includes a coil seat 807, centering around an axial direction C and being wound with a coil 808 while electrically connecting the coil 808 to the external power supply. It is noted that the assembly of the coil seat 807 and the coil 808 forms a coil set. Moreover, the top module 800a further comprises: a magnet set and; and a conducting seat 803. Wherein, the magnet set is further comprised of: an inner magnet ring 804; and an outer magnet ring 805, ensheathing the inner magnet ring 804, by which the coil 808 is sandwiched between the inner magnet ring 804 and the outer magnet ring 805. Moreover, the conducting seat 803 is disposed surrounding the exterior of the outer magnet ring 805 for conducting the magnetic force. It is noted that the inner and the outer magnet rings 804, 805 can be made of permanent magnet while the conducting seat 803 can be a magnetic dust core. Furthermore, the assembly of the inner magnet ring 804, the outer magnet ring 805 and the conducting seat 803 forms a stator set, and the integration of the coil set and the stator set forms a motor set.

The top module 800a further comprises a guide rail 806, made of a metal of high rigidity. The guide rail 806 is disposed at the bottom of the conducting seat 803 and is extending along a direction that is parallel with the axial direction C. In addition, the guide rail 806 is extending into the enclosure formed inside the coil seat 807 and coupled thereto for guiding the coil seat 807 to perform a reciprocating movement. For promoting the reciprocating movement, a top elastic member 809, being substantially a spring or other resilience elements, is disposed between the conducting seat 803 and the coil seat 807 in a manner that the top elastic member 809 is mounted on the guide rail 806. Furthermore, the top module 800a further comprises a fixed seat 801, being arranged at a position separating from the conducting seat 803 by an accommodation space for allowing the coil module, composed of the coil seat 807 and the coil 808, to be received therein. The fixed seat 801 is configured with a via hole 8011 for allowing the bottom of the coil seat 807 to extend out of the fixed seat 801 therefrom. As shown in FIG. 2, there is a flange 8071 formed on an outer sidewall of the coil seat 807 in a manner that the outer diameter of the flange 8071 is larger than the inner diameter of the via hole 8011 of the fixed seat 801 for using the flange 8071 to restrict the coil seat 807 inside the accommodation space formed between the fixed seat 801 and the conducting seat 803 without departing.

It is noted that the assembly of the fixed seat 801 and the conducting seat 803 can be received inside by a casing 802 that it can be made of a plastic. In an exemplary embodiment of the invention, a movable part 810 is formed on the exterior of the casing 802 which is substantially a ring, being formed with an internal thread 8101 on the inner side wall thereof.

The bottom module 800b comprises a base 817. As shown in FIG. 2, the upward extending portion of the base 817 forms a fixed part 8173, being formed with an external thread 8174 on the outer side wall thereof. As the external thread 8174 of the fixed part 8173 can be screwed with the internal thread 8101 of the moveable part 810 so that the top module 800a and the bottom module 800b can be connected with each other in a detachable manner. However, the detachable connection mechanism composed of the internal thread 8101 and the external thread 8174 is used primarily for enabling the top module 800a and the bottom module 800b can be connected with each other in a detachable manner, so that other detachable connection mechanism such as latches, wedge sets, and so on, are all considered to be variation of the aforesaid embodiment and thus are not to be regarded as a departure from the spirit and scope of the invention.

As shown in FIG. 2, the base 817 is configured with a channel for enabling objects to flow in and out the base therefrom. In an exemplary embodiment, the channel comprises at least an inlet 8171 and at least an outlet 8172, disposed symmetrically at the sides of the base 817. The inlet 8171 is configured with an entrance 8171a and a terminal 8171b in a manner that objects can flow into the base 817 through the entrance 8171a. There is a one-ways suction valve 812 arranged at the terminal 8171b which is shaped like a membrane covering the terminal 8171b from the outside thereof. Thereby, once objects flow pass the one-way suction valve 812, it is prevented from backward flowing into the inlet 8171. Similarly, the outlet 8172 is configured with an entrance 8172a and a terminal 8172b in a manner that there is an one-way drain valve 818 disposed at the entrance 8172a which is shaped like a membrane covering the entrance 8172a of the outlet 8172 form the inside thereof. Thereby, once objects flow pass the one-way drain valve 818 and into the outlet 8172, it is prevented from backward flowing into the base 817.

For clarity, the amount, positions and shapes of the inlet 8171 and the outlet 8172 are designed according to actual requirement and thus are not limited by the aforesaid embodiment, which is also true for the one-way suction valve 812 and the one-way drain valve 818. In this embodiment, the one-way suction valve 812 and the one-way drain valve 818 are all made of a rubber and are integrally formed with the inlet 8171 and the outlet 8172 in respective for achieving purposes of light weight, small size and cost down. Both of the one-way suction valve 812 and the one-way drain valve 818 can be secured on the base 817 by a compressed unit 8181.

As shown in FIG. 2, the bottom module 800b has a bottom elastic member 811, which is disposed inside the base 817. In this embodiment, both the top and bottom elastic members 809, 811 are substantially springs and being arranged at positions with respect to the same axis. Moreover, there is a diaphragm element 820 being received in the base 817 in a manner that it is arranged to cover the bottom elastic member 811 as it is made of material with resilience such as rubber. In addition, the base 817 further comprises a top seat 819 which can be fused and integrated with the base 817 by ultrasonic welding. By mounting the top seat 819 on the fixed part 8173, the diaphragm element 820 can be clamped by the compressed unit 8181 inside the base 817 so that the diaphragm element 820 is restricted inside the bottom module 800b without departing.

Moreover, there is a buffering pad 814, being shaped like a downward-opening trumpet and made of a flexible silicon gel material, which is disposed at the bottom of the base 817. The buffering pad 814 is configured with: an air channel 816, for enabling air to flow from the top of the buffering pad 814 into the same while having a filter being received therein; and a tube 815 formed in communication with the inlet 8171 of the base 817 for extending the length of the inlet 8171. It is noted that the filter received inside the air channel 816 can be made of activated carbon filter, oxygen enrichment membrane, molecule sieve or the combination thereof.

As shown in FIG. 3, by screwing the movable part 810 onto the fixed part 8173, the top module 800a and the bottom module 800b are assembled and form a detachable pump 800, in which the bottom of the coil seat 807 is abutted against the diaphragm element 820 for enabling the diaphragm element 820 to be deformed by the pressing of the counter reacting top and bottom elastic members 809, 811. When a current is conducted through the coil 808, the coil set is subjected to a force and thus moves up and down along the axial direction C in the casing in synchronization with the alternating of the current; and the same time that the bottom elastic member 811 and the top elastic member 809 are pressed opposite to each other that are caused by the reciprocating movement of the coil set, and thus propelling the diaphragm element 820 to vibrate accordingly and creating suction for the detachable pump. Ideally, the resilience of the top elastic member 809 is balanced with that of the bottom elastic member 811, so that the vibration of the diaphragm element 820 can be maintained in a uniform manner.

Figure 4:
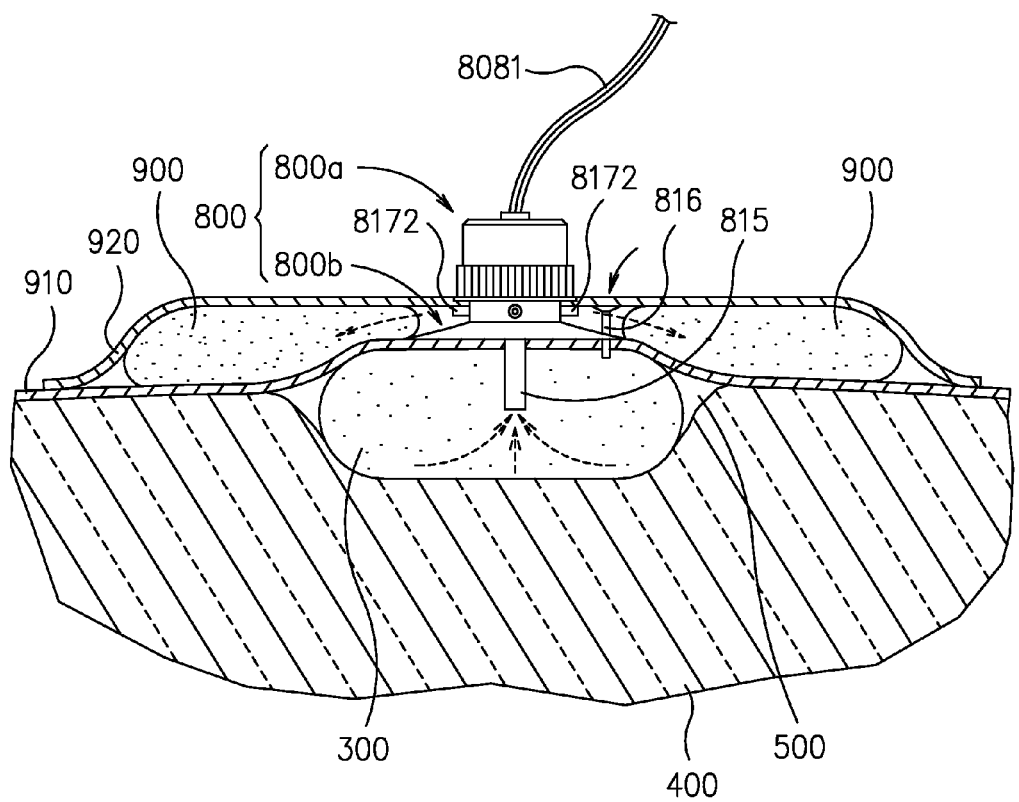
FIG. 4 is a schematic diagram showing a negative pressure wound therapy system using a detachable pump according to the present invention.

Please refer to FIG. 4, which is a schematic diagram showing a negative pressure wound therapy system using a detachable pump according to the present invention. In FIG. 4, a detachable pump 800 of the invention is adapted for a negative pressure wound therapy system in cooperation with a dressing 300 and an absorbent material 900, in which the dressing 300 is placed on a wound 500 of a flesh 400 for absorbing spent liquid, and the dressing 300 and the absorbent material 900 is insulated by a layer of water-resisting material 910. It is noted that at least a side of the water-resisting layer 910 is adhesive for attaching the same to the flesh 400. The bottom module 800b is placed on the dressing 300 in a manner that the buffering pad 814 is in close contact with the water-resisting layer 910 for providing airtight, leaking prevention and collision proof, while the tube 815 inside the buffering pad 814 is directed to penetrate the water-resisting layer 910 and inserted into the dressing 300. In addition, the absorbent material 900 is arranged at a position corresponding to the outlet 8172 of the detachable pump 8000 while covering the absorbent material 900 with a layer of ventilating material 920. Finally, the top module 800a is screwed to the bottom module 800bso as to complete the negative pressure wound therapy system.

In this exemplary embodiment, the detachable pump 800 is connected to an external power source by a power line 8081, which is electrically connected to the coil 808 of the top module 800a, as shown in FIG. 2 and FIG. 3. As soon as the power line 8081 is connected to the power source, the detachable pump can be activated for drawing spent liquid absorbed by the dressing 300 to flow into the detachable pump 800 through the tube 815 and thereafter drain such spent liquid through the outlet 8172 for the absorbent material 900 to absorb.

During the drawing and draining, as the dressing 300 and the wound 500 are insulted from the detachable pump 800 by the water-resisting layer 910, the spent liquid can be prevented from flowing back into the wound 500. In addition, as the water-resisting layer 910 can be tightly secured to the flesh 400, a negative pressure can be maintained on the wound 500. The use of the ventilating material 920 is to prevent the discomfort caused by the inflation of the absorbent material 900 during the drawing and draining. Moreover, as the air channel 816 is in communication with atmosphere, not only it is working for preventing the wound from subjecting an overly negative pressure, but also it can bring fresh air to the wound 500 and the dressing 300 for suppressing anaerobic bacteria and the phagocytosis of white blood cell. When the absorbent material 900 is soaked with spent liquid, the top module 800a can be detached for removing and the replacing the bottom module 800b, the dressing 300 and the absorbent material 900. That is, the motor portion of the detachable pump can be use repetitively for cost saving.

Figure 5:
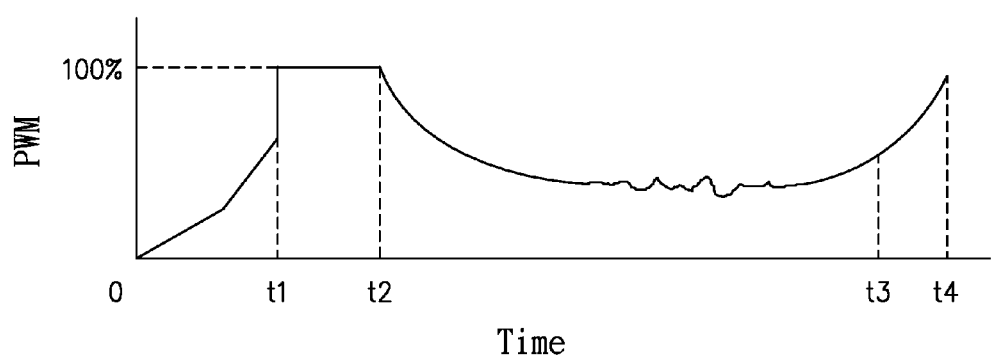
FIG. 5 is a line chart depicting the output power of a detachable pump as it is being applied in a negative pressure wound therapy system of the invention.

As the detachable pump 800 adopts a voice coil linear motor, not only it can be designed with less parts, but also it can increase a vibration frequency of the diaphragm to near ultrasonic range and thus reduce noise noticeable by human ear. Moreover, it is noted that the higher the working frequency is, the higher the power density of a motor will be, so that under the same power requirement, the size of the motor used in the detachable pump 800 can be reduced. As for the pressure sensing, the detachable pump 800 of the invention adopts a semi-close loop for sensor-less control. Please refer to FIG. 5, which is a line chart depicting the output power of a detachable pump 800 as it is being applied in a negative pressure wound therapy system of the invention. As shown in FIG. 5, before an initial operating time t1, the detachable pump 800 is in slow start mode for reducing in-rush current; and then the pump is driven to operate in maximum power for a period of time, as the period defined between t1 and t2, for increasing the negative pressure subjecting to the wound 500 until it is larger than a predefined value; and then the negative pressure is stabilized to the predefined value by pulse-width modulation (PWM) control during the period between t2 and t3. During the stabilization period, if there is a leak, except for the PWM control, the voice coil frequency should be adjusted for flow regulation so as to compensate the leak and pressure drop without changing the target PWM control. It is noted that since the close loop uses only current feed-back and no pressure sensor as pressure feed-back for stabilizing pressure, it is referred as semi-close loop sensor-less control. Moreover, when the absorbent material is soaked with spent liquid, the detachable pump will not be able to suck in any more spent liquid and thus cause current to increase, as shown in the period between t3 and t4, the controller of the pump will stop the operation of the pump automatically and issue an alert after the period of increased and unstable current exceeds a period of time, thereby, no such full-spent-liquid alert circuit is required so that the design of the detachable pump can be effectively simplified and thus the manufacturing cost of the same can be reduced.

Figure 6:
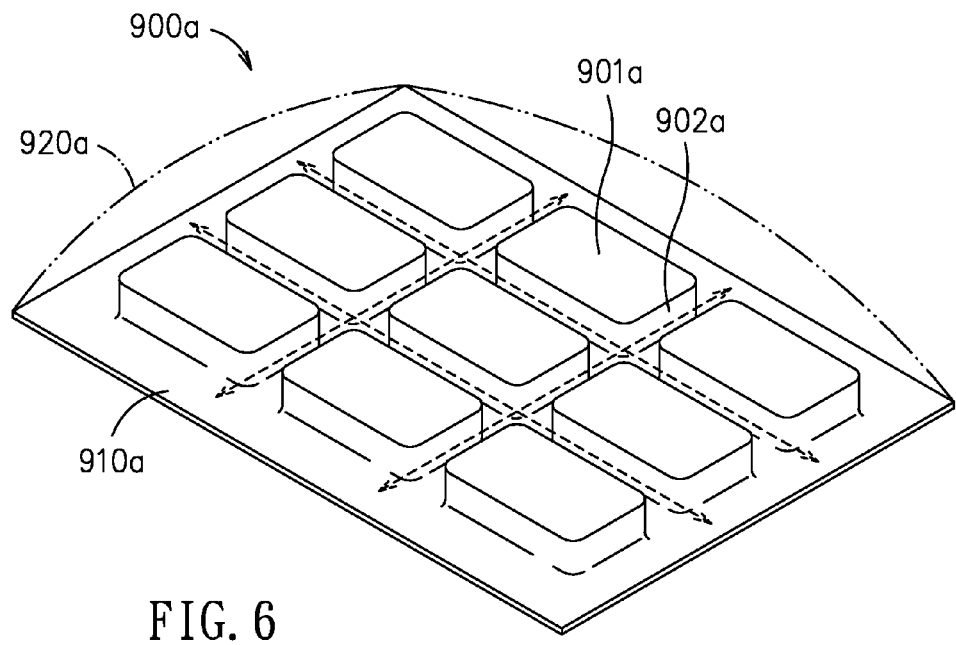
FIG. 6 is a three-dimensional diagram showing an absorbent material used in a negative pressure wound therapy system of the invention.

Please refer to FIG. 6, which is a three-dimensional diagram showing an absorbent material used in a negative pressure wound therapy system of the invention. The absorbent material 900a of FIG. 6 is featuring in that: there are a plurality of protruding structures 901a being formed inside the absorbent material 900a in a manner that the plural protruding structures 901a are formed on the water-resisting layer 910a while forming channels 902a in communication with each other and covering the plural protruding structures 901a with a ventilating material 920a. Thereby, spent liquid can be draw to each of the protruding structure 901a uniformly through the channels 902a for enhancing the absorption of the absorbent material 900a. In addition, be designing channels 902a on the absorbent material 900a, the flexibility of the absorbent material 900a can be improved and thus can be closely attached to the wounded part of a patient. In addition, the absorbent material 900a can be cut into pieces with shape and capacity matching with the estimated amount of spent liquid of a wound 500. As for the water-resisting layer 910a and the ventilating material 920a, they are working similar to those described in FIG. 4 and thus are not described further herein.

Figure 7:
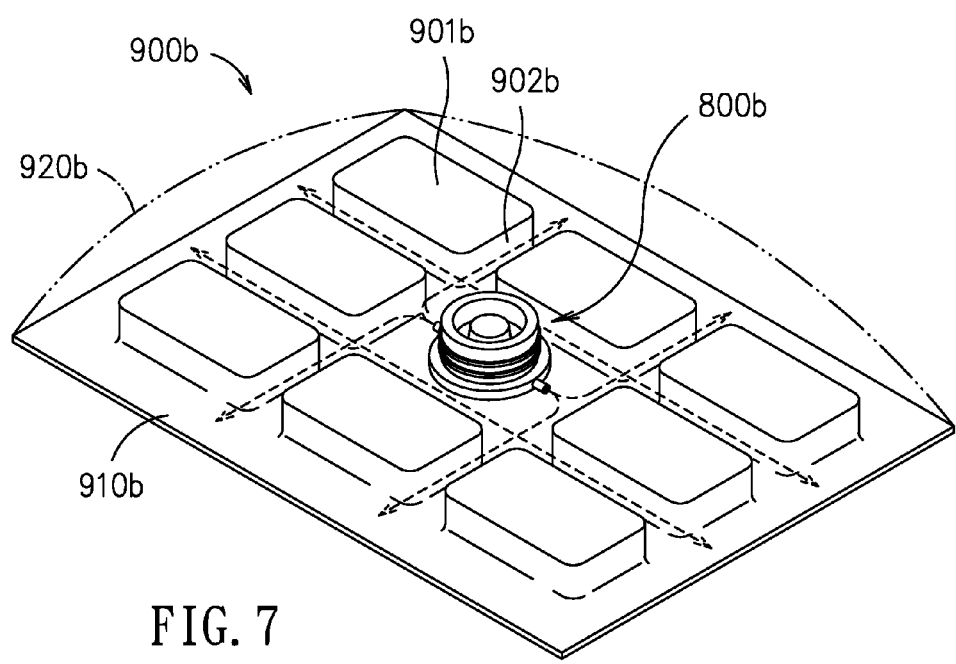
FIG. 7 is a three-dimensional diagram showing a bottom module with integrally formed absorbent material.

Please refer to FIG. 7, which is a three-dimensional diagram showing a bottom module 800b with integrally formed absorbent material 900b. Similar to that shown in FIG. 6, the absorbent material 900b is also configured with a plurality of protruding structures 901b which are formed in a manner that the plural protruding structures 901b are formed on the water-resisting layer 910b while forming channels 902b in communication with each other and covering the plural protruding structures 901b with a ventilating material 920b. The characteristic of the absorbent material 900b shown in FIG. 7 is that: the absorbent material 900b is integrally formed with the bottom module 800b. Thereby, as the soaked absorbent material 900b can be disposed along with the contaminated bottom module 800b at the same time, the convenience of replacing contaminated parts for the detachable pump is enhanced.

To sum up, the present invention provides a detachable pump configured with disposable components that can be incorporated into a negative pressure wound therapy (NPWT) system along with dressings and absorbent materials for drawing spent liquid of a wound to be absorbed directly by the absorbent materials by way of the dressings so that not only the piping length and the volume of the NPWT system are reduced, but also the power requirement of the pump is decreased. In addition, with respect to the shortcomings of those conventional wound therapy systems, the present invention provide a personal, miniature wearable wound therapy system that is lighter and less power consuming and is suitable for ambulatory patient as well as daily care for all kinds of open wounds without affecting the daily operation of the patient.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A detachable pump, comprising:
a top module, including:
a motor set, electrically connected to an external power supply for providing motive force; and
at least a top elastic member, capable of being driven to move in reciprocation by the motor set; and
a bottom module, arranged beneath the top module in a manner that it is connected to the top module by a detachable connection mechanism, comprised of:
a base, configured with a channel for enabling fluid to flow in and out of the base therefrom;
at least a single one-way valve, installed in the channel for preventing fluid flow in a direction toward the base;
a diaphragm element, being received inside the base; and
at least a bottom elastic member, capable of elastically countering the resilience of the top elastic member caused by the reciprocating movement of the top elastic member and thus propelling the diaphragm element to move accordingly to create suction;
wherein the detachable connection mechanism comprises:
a moveable part, arranged on the top module, having a moving threaded section, being free to move in relation to the top module; and
a fixed part arranged on the bottom module, immovably fixed to the bottom module, having a threaded section capable of being screwed into the moving threaded section of the movable part;
wherein the diaphragm is located within a circumferential boundary of the threaded section on the fixed part;
wherein the detachable pump provides a negative pressure causing fluid to be drawn into and exhausted by the detachable pump.

2. The detachable pump of claim 1, wherein the motor set further comprising:
a coil module, including a coil seat being wound with a coil while electrically connecting the coil to the external power supply; and
a stator module, further comprising:
a magnet set, for exerting a magnetic force to the coil module; and
a conducting seat, disposed surrounding the exterior of the coil module for conducting the magnetic force.

3. The detachable pump of claim 1, wherein the channel further comprises:
at least one inlet, provided for fluid to enter the bottom module therefrom; and
at least one outlet, provided for fluid to exit the base.

4. The detachable pump of claim 3, wherein the at least a single one-way valve of the bottom module further comprises:
at least a single one-way suction valve, disposed at an end of the at least one inlet for allowing fluid only to flow into the bottom module through the at least one inlet while preventing fluid from flowing back from the bottom module into the at least one inlet; and
at least a single one-way drain valve, disposed at an end of the at least one outlet for allowing fluid in the bottom module only to flow into the at least one outlet therethrough and thus being drained from the base while preventing fluid from flow back into the base.

5. The detachable pump of claim 4, wherein the inlet is configured with an inlet entrance and an inlet terminal in a manner that the at least a single one-way suction valve seals the inlet terminal from the exterior of the base; and the outlet is configured with an outlet entrance and an outlet exit in a manner that the at least a single one-way drain valve seals the outlet entrance of the outlet from the interior of the base.

6. The detachable pump of claim 1, wherein the movable part is ring shaped, wherein the moving threaded section is an internal thread and mounted on the moveable part of the top module; and the fixed part is formed with an external thread and is arranged on the base on the bottom module.

7. The detachable pump of claim 2, wherein the top module further comprises: a guide rail, arranged at the bottom of the conducting seat in a manner that it extends into an enclosure formed inside the coil seat in a direction parallel to the reciprocating movement of the top elastic member while mounting the top elastic member on the guide rail.

8. The detachable pump of claim 2, wherein the top module further comprises:
   a fixed seat, separable from the conducting seat having an accommodation space for allowing the coil module to be received therein; and having a through hole formed therein for allowing the bottom of the coil seat to extend out of the fixed seat.

9. The detachable pump of claim 8, wherein a flange is formed on an outer sidewall of the coil seat in a manner that the outer diameter of the flange is larger than the inner diameter of the through hole of the fixed seat, wherein the flange confines the coil seat inside the accommodation space.

10. The detachable pump of claim 2, wherein the magnet set further comprises:
    an inner magnet ring; and
    an outer magnet ring, ensheathing the inner magnet ring while sandwiching the coil between the inner magnet ring and the outer magnet ring.

11. The detachable pump of claim 1, wherein the base further comprises:
    a buffering pad, being trumpet shaped and dilated toward the bottom of the base, configured with: an air channel, for enabling air to flow from the top of the buffering pad into the same; and a tube formed in communication with an inlet of the base.

12. The detachable pump of claim 1, wherein the base further comprises a top seat mounted on the diaphragm element so that the diaphragm element is restricted inside the bottom module.

13. The detachable pump of claim 1, wherein both the top and bottom elastic members are springs that are arranged coaxially.

* * * * *